US009246356B2

(12) United States Patent
Baarman

(10) Patent No.: US 9,246,356 B2
(45) Date of Patent: Jan. 26, 2016

(54) ADAPTIVE INDUCTIVE POWER SUPPLY

(75) Inventor: David W. Baarman, Fennville, MI (US)

(73) Assignee: ACCESS BUSINESS GROUP INTERNATIONAL LLC, Ada, MI (US)

( * ) Notice: Subject to any disclaimer, the term of this patent is extended or adjusted under 35 U.S.C. 154(b) by 0 days.

(21) Appl. No.: 13/524,575

(22) Filed: Jun. 15, 2012

(65) Prior Publication Data

US 2012/0249097 A1  Oct. 4, 2012

Related U.S. Application Data

(63) Continuation of application No. 13/078,094, filed on Apr. 1, 2011, which is a continuation of application No. 12/615,393, filed on Nov. 10, 2009, which is a continuation of application No. 11/684,860, filed on Mar. 12, 2007, now Pat. No. 7,639,514, which is a continuation of application No. 10/689,499, filed on Oct. 20, 2003, now Pat. No. 7,212,414.

(60) Provisional application No. 60/444,794, filed on Feb. 4, 2003.

(51) Int. Cl.
*H02M 3/335* (2006.01)
*H02J 13/00* (2006.01)
(Continued)

(52) U.S. Cl.
CPC ............... *H02J 13/0075* (2013.01); *A61L 2/10* (2013.01); *C02F 1/008* (2013.01); *C02F 1/325* (2013.01); *C02F 9/005* (2013.01); *H02J 5/005* (2013.01); *H02J 13/0086* (2013.01); *H02M 3/33523* (2013.01); *H02M 3/33569* (2013.01); *H02M 3/33576* (2013.01); *H02M 7/53803* (2013.01); *H05B 37/03* (2013.01); *H05B 41/36* (2013.01); *C02F 1/001* (2013.01); *C02F 2201/326* (2013.01); *C02F 2201/3228* (2013.01); *C02F 2209/005* (2013.01); *C02F 2209/008* (2013.01); *C02F 2209/40* (2013.01); *H02J 7/0027* (2013.01); *H02M 2007/4815* (2013.01);
(Continued)

(58) Field of Classification Search
CPC ...... H02M 3/335–3/33576; H02M 2007/4815; H02M 2007/4818
USPC ........ 363/16, 21.01, 39–41, 97, 131; 324/429
See application file for complete search history.

(56) References Cited

U.S. PATENT DOCUMENTS 4,076,996 A   2/1978   Maehara et al.
4,639,714 A   1/1987   Crowe
(Continued)

FOREIGN PATENT DOCUMENTS

DE   4233861   4/1994
EP   0178852   4/1986
(Continued)

OTHER PUBLICATIONS

U.S. Appl. No. 13/450,522 Office Action dated Jul. 17, 2012.
(Continued)

*Primary Examiner* — Jessica Han
(74) *Attorney, Agent, or Firm* — Warner Norcross and Judd LLP

(57) ABSTRACT

A contactless power supply has a dynamically configurable tank circuit powered by an inverter. The contactless power supply is inductively coupled to one or more loads. The inverter is connected to a DC power source. When loads are added or removed from the system, the contactless power supply is capable of modifying the resonant frequency of the tank circuit, the inverter frequency, the inverter duty cycle or the rail voltage of the DC power source.

29 Claims, 6 Drawing Sheets

(51) Int. Cl.

| | | |
|---|---|---|
| *A61L 2/10* | (2006.01) | |
| *C02F 1/32* | (2006.01) | |
| *C02F 9/00* | (2006.01) | |
| *H02J 5/00* | (2006.01) | |
| *H02M 7/538* | (2007.01) | |
| *H05B 37/03* | (2006.01) | |
| *H05B 41/36* | (2006.01) | |
| *C02F 1/00* | (2006.01) | |
| *H02J 7/00* | (2006.01) | |
| *H02M 7/48* | (2007.01) | |

(52) U.S. Cl.
CPC .... *H02M2007/4818* (2013.01); *Y02B 70/1433* (2013.01); *Y02B 70/1441* (2013.01)

(56) References Cited

U.S. PATENT DOCUMENTS

| | | |
|---|---|---|
| 4,641,126 A | 2/1987 | Crowe |
| 4,644,321 A | 2/1987 | Kennon |
| 4,675,648 A | 6/1987 | Roth et al. |
| 4,914,539 A | 4/1990 | Turner et al. |
| 5,070,293 A | 12/1991 | Ishii et al. |
| 5,122,729 A | 6/1992 | Itoga et al. |
| 5,187,414 A | 2/1993 | Fellows et al. |
| 5,241,160 A | 8/1993 | Bashan et al. |
| 5,298,836 A | 3/1994 | Backmund et al. |
| 5,325,046 A | 6/1994 | Young et al. |
| 5,367,242 A | 11/1994 | Hulman |
| 5,406,174 A | 4/1995 | Slegers |
| 5,440,300 A | 8/1995 | Spillman, Jr. |
| 5,446,346 A | 8/1995 | Nilssen |
| 5,450,305 A | 9/1995 | Boys et al. |
| 5,455,466 A | 10/1995 | Parks et al. |
| 5,476,488 A | 12/1995 | Morgan et al. |
| 5,495,405 A | 2/1996 | Fujimura et al. |
| 5,500,792 A | 3/1996 | Jeon et al. |
| 5,521,590 A | 5/1996 | Hanaoka et al. |
| 5,559,507 A | 9/1996 | Beigel |
| 5,586,017 A | 12/1996 | Rohrbeck et al. |
| 5,587,573 A | 12/1996 | Owen et al. |
| 5,596,567 A | 1/1997 | deMuro et al. |
| 5,638,402 A | 6/1997 | Osaka et al. |
| 5,644,286 A | 7/1997 | Brosh et al. |
| 5,734,254 A | 3/1998 | Stephens |
| 5,757,144 A | 5/1998 | Nilssen |
| 5,777,861 A | 7/1998 | Shimizu et al. |
| 5,796,334 A | 8/1998 | Chen et al. |
| 5,814,900 A | 9/1998 | Esser et al. |
| 5,818,127 A | 10/1998 | Abraham |
| 5,831,348 A | 11/1998 | Nishizawa |
| 5,889,384 A | 3/1999 | Hayes et al. |
| 5,905,372 A | 5/1999 | Kuffner et al. |
| 5,917,429 A | 6/1999 | Otis, Jr. et al. |
| 5,929,604 A | 7/1999 | Irvin |
| 5,963,012 A | 10/1999 | Garcia et al. |
| 5,982,276 A | 11/1999 | Stewart |
| 5,982,764 A | 11/1999 | Palermo et al. |
| 6,028,413 A * | 2/2000 | Brockmann .................. 320/108 |
| 6,040,986 A | 3/2000 | Sakamoto et al. |
| 6,072,362 A | 6/2000 | Lincoln |
| 6,118,249 A | 9/2000 | Brockmann et al. |
| 6,141,227 A | 10/2000 | Sheikh et al. |
| 6,151,222 A | 11/2000 | Barrett |
| 6,157,258 A | 12/2000 | Adishian et al. |
| 6,173,899 B1 | 1/2001 | Rozin |
| 6,181,082 B1 | 1/2001 | Moisin |
| 6,184,651 B1 | 2/2001 | Fernandez et al. |
| 6,191,537 B1 | 2/2001 | Celso |
| 6,211,799 B1 | 4/2001 | Post et al. |
| 6,212,430 B1 | 4/2001 | Kung |
| 6,255,635 B1 | 7/2001 | Thompson et al. |
| 6,262,897 B1 | 7/2001 | Yasumura |
| 6,271,508 B1 | 8/2001 | Thompson et al. |
| 6,273,022 B1 | 8/2001 | Pu et al. |
| 6,285,567 B1 | 9/2001 | Kennedy |
| 6,301,128 B1 | 10/2001 | Jang et al. |
| 6,307,468 B1 | 10/2001 | Ward, Jr. |
| 6,316,756 B1 | 11/2001 | Thompson et al. |
| 6,348,679 B1 | 2/2002 | Ryan et al. |
| 6,359,267 B1 | 3/2002 | Wilcox et al. |
| 6,366,817 B1 | 4/2002 | Kung |
| 6,400,991 B1 | 6/2002 | Kung |
| 6,415,388 B1 | 7/2002 | Browning et al. |
| 6,427,065 B1 | 7/2002 | Suga et al. |
| 6,430,064 B1 | 8/2002 | Tsuchimoto et al. |
| 6,436,299 B1 | 8/2002 | Baarman |
| 6,437,521 B1 | 8/2002 | Pienisaari |
| 6,442,434 B1 | 8/2002 | Zarinetchi et al. |
| 6,452,482 B1 | 9/2002 | Cern |
| 6,462,432 B1 | 10/2002 | Seelig et al. |
| 6,472,827 B1 | 10/2002 | Nilssen |
| 6,483,721 B2 | 11/2002 | Terashi |
| 6,498,456 B2 | 12/2002 | Ettes et al. |
| 6,504,318 B1 | 1/2003 | Pienisaari |
| 6,521,874 B2 | 2/2003 | Thompson et al. |
| 6,548,985 B1 | 4/2003 | Hayes et al. |
| 6,600,142 B2 | 7/2003 | Ryan et al. |
| 6,615,023 B1 | 9/2003 | Ehrensvärd |
| 6,617,557 B1 | 9/2003 | Ryan et al. |
| 6,636,146 B1 | 10/2003 | Wehoski |
| 6,649,888 B2 | 11/2003 | Ryan et al. |
| 6,654,259 B2 | 11/2003 | Koshita et al. |
| 6,664,881 B1 | 12/2003 | Thompson et al. |
| 6,703,920 B2 | 3/2004 | Zimmer |
| 6,730,894 B2 | 5/2004 | Thompson et al. |
| 6,751,691 B1 | 6/2004 | Douglas |
| 6,756,697 B2 | 6/2004 | Mizutani et al. |
| 6,765,959 B1 | 7/2004 | Tanaka et al. |
| 6,791,302 B2 | 9/2004 | Tang et al. |
| 6,807,070 B2 * | 10/2004 | Ribarich .................. 363/17 |
| 6,812,445 B2 | 11/2004 | Gorbold |
| 6,825,620 B2 | 11/2004 | Kuennen et al. |
| 6,844,702 B2 | 1/2005 | Giannopoulos et al. |
| 6,861,629 B2 | 3/2005 | Dahake et al. |
| 6,912,137 B2 | 6/2005 | Berghegger |
| 6,934,167 B2 | 8/2005 | Jang et al. |
| 6,995,345 B2 | 2/2006 | Gorbold |
| 7,062,331 B2 | 6/2006 | Zarinetchi et al. |
| 7,065,658 B1 | 6/2006 | Baraban et al. |
| 7,110,269 B2 | 9/2006 | Cao et al. |
| 7,155,291 B2 | 12/2006 | Zarinetchi et al. |
| 7,212,414 B2 | 5/2007 | Baarman |
| 7,489,530 B2 | 2/2009 | Paull |
| 7,522,878 B2 | 4/2009 | Baarman |
| 7,551,011 B2 | 6/2009 | Paull |
| 7,626,463 B2 | 12/2009 | Paull |
| 7,639,514 B2 | 12/2009 | Baarman |
| 7,804,045 B2 | 9/2010 | Rosenbloom et al. |
| 2001/0017781 A1 | 8/2001 | Hideaki |
| 2001/0052843 A1 | 12/2001 | Wiesman et al. |
| 2002/0017878 A1 | 2/2002 | Hakuta et al. |
| 2002/0118004 A1 | 8/2002 | Scheible et al. |
| 2002/0130642 A1 | 9/2002 | Ettes et al. |
| 2002/0154518 A1 | 10/2002 | Elferich et al. |
| 2003/0006880 A1 | 1/2003 | Zimmer |
| 2003/0015479 A1 | 1/2003 | Kuennen et al. |
| 2003/0210106 A1 | 11/2003 | Cheng et al. |
| 2003/0214821 A1 | 11/2003 | Giannopoulos et al. |
| 2004/0130915 A1 | 7/2004 | Baarman |
| 2004/0130916 A1 | 7/2004 | Baarman |
| 2004/0145342 A1 | 7/2004 | Lyon |
| 2005/0007067 A1 | 1/2005 | Baarman et al. |
| 2007/0109708 A1 | 5/2007 | Hussman et al. |
| 2008/0211478 A1 | 9/2008 | Hussman et al. |
| 2010/0171367 A1 | 7/2010 | Kitamura et al. |

FOREIGN PATENT DOCUMENTS

| | | |
|---|---|---|
| EP | 0267009 | 5/1988 |
| EP | 1 209 791 | 5/2002 |
| GB | 2124042 | 2/1984 |
| GB | 2 347 801 | 9/2000 |
| GB | 2388715 | 11/2003 |

(56) References Cited

FOREIGN PATENT DOCUMENTS

| | | |
|---|---|---|
| GB | 2388716 | 11/2003 |
| JP | 5978496 | 5/1984 |
| JP | 6196699 | 5/1986 |
| JP | 04183274 | 6/1992 |
| JP | H06-113478 | 4/1994 |
| JP | H06-133476 | 5/1994 |
| JP | 07153577 | 6/1995 |
| JP | 7507917 | 8/1995 |
| JP | 8506927 | 7/1996 |
| JP | H8214473 | 8/1996 |
| JP | 8298778 | 11/1996 |
| JP | H08-340650 | 12/1996 |
| JP | 09103037 | 4/1997 |
| JP | H09-149565 | 6/1997 |
| JP | 09266081 | 10/1997 |
| JP | 10012197 | 1/1998 |
| JP | 10041089 | 2/1998 |
| JP | 10225129 | 8/1998 |
| JP | H10-225020 | 8/1998 |
| JP | H10215530 | 8/1998 |
| JP | 10-258129 | 9/1998 |
| JP | H10-233235 | 9/1998 |
| JP | H1118813 | 7/1999 |
| JP | H11155245 | 7/1999 |
| JP | 2000-270501 | 9/2000 |
| JP | 2000295796 | 10/2000 |
| JP | 2001128375 | 5/2001 |
| JP | 2001238372 | 8/2001 |
| JP | 2002-272134 | 9/2002 |
| JP | 2003-018847 | 1/2003 |
| WO | 89/10030 | 10/1989 |
| WO | 9419919 | 9/1994 |
| WO | 9422209 | 9/1994 |
| WO | 9428560 | 12/1994 |
| WO | 9605648 | 2/1996 |
| WO | 9617499 | 6/1996 |
| WO | 0054387 | 9/2000 |
| WO | 0078678 | 12/2000 |
| WO | 01/28629 | 4/2001 |
| WO | 02/37641 | 5/2002 |
| WO | 03096361 | 11/2003 |

OTHER PUBLICATIONS

Notice of Allowance for U.S. Appl. No. 13/450,522 mailed May 30, 2013.
US 4,658,187, 4/1987, Grubbs (withdrawn).
Current Control of Quantum Series Resonant Inverter and Application for a DC Motor Drive, Korea Advanced Institute of Science and Technology since 1971, Advisor: Myung Joong Youn by Gun-Woo Moon, Department fo Electrical Engineering Korea Advanced Institute of Science and Technology, Dec. 28, 1991.
Malik E. Elbuluk, Member IEEE, George C. Verghese, member IEEE, and John G. Kassakian, Senior Member, IEEE, Sampled-Data Modeling and Digital Control of Resonant Converters, IEEE Transactions on Power Electronics, vol. 3, No. 3 Jul. 1988.
Gyu B. Joung, Chun T. Rim, and Gyu H. Cho, Integral Cycle Mode Control of the Series Resonant Converter, IEEE Transactions on Power Electronics, vol. 4, No. 1, Jan. 1989.
U.S. Appl. No. 13/450,522, Office Action dated Jul. 17, 2012.
Gulko, M. et al., "Inductor-Controlled Current-Sourcing Resonant Inverter and its Application as a High Pressure Discharge Lamp Driver", IEEE, Feb. 13, 1994, pp. 434-440.

* cited by examiner

ADAPTIVE INDUCTIVE POWER SUPPLY

This application incorporates by reference the following references: U.S. Pat. No. 7,522,878 to Baarman, which is entitled "Adaptive Inductive Power Supply with Communication" and issued Apr. 21, 2009; U.S. Pat. No. 7,132,918 to Baarman et al., which is entitled "Inductive Coil Assembly" and issued Nov. 7, 2006; U.S. application Ser. No. 10/689,154 to Baarman, which is entitled "Electrostatic Charge Storage Assembly" and filed on Oct. 20, 2003; and U.S. Pat. No. 7,518,267 to Baarman, which is entitled "Adapter" and issued Apr. 14, 2009.

BACKGROUND OF THE INVENTION

This invention relates generally to contactless power supplies, and more specifically to inductively coupled contactless power supplies.

Contactless energy transmission systems (CEETS) transfers electrical energy from one device to another without any mechanical connection. Because there is no mechanical connection, CEETS have many advantages over conventional energy systems. They are generally safer because there is little danger of sparks or electric shocks due to the isolation of the power supply. They also tend to have a longer life since there are no contacts to become worn. Due to these advantages, CEETS have been used in everything from toothbrushes to portable telephones to trains.

CEETS are composed of power supplies and remote devices. The remote devices could be chargeable, such as batteries, micro-capacitors, or any other chargeable energy source. Alternatively, CEETS could directly power the devices.

One kind of CEETS uses magnetic induction to transfer energy. Energy from a primary winding in the power supply is transferred inductively to a secondary winding in the chargeable device. Because the secondary winding is physically spaced from the primary winding, the inductive coupling occurs through the air.

Without a physical connection between the primary winding and the secondary winding, conventional feedback control is not present. Thus, control of the energy transfer in a CEETS from the primary to the secondary is difficult.

One common solution is to design a CEETS dedicated to one type of device. For example, a CEETS for a rechargeable toothbrush is designed only for recharging a toothbrush, while a CEETS for a rechargeable telephone works only with a specific type of telephone. While this solution allows the CEET to operate effectively with one particular device, it fails to be sufficiently flexible to allow the power supply to operate with different rechargeable devices.

Obviously, making a CEETS for each specific chargeable device is costly and inefficient. Thus, a system for contactless energy transmission which is efficient and can be used with a large variety of devices is highly desirable.

SUMMARY OF THE INVENTION

The aforementioned problems are overcome in the present invention.

A contactless power supply inductively couples by way of a tank circuit to a device. The power supply has a controller for dynamically adjusting the resonant frequency of the tank circuit. The tank circuit could have either a variable capacitor or a variable inductor, or both. In one embodiment, the power supply also may have an inverter. A drive circuit connected to the inverter controls the frequency of the inverter and the duty cycle of the inverter. A controller with an attached memory directs the operation of the inverter by way of the drive circuit. Alternatively, The inverter may also be connected to a DC power source. The controller could then change the rail voltage of the DC power source.

By altering the resonant frequency of the tank circuit, the frequency of the inverter, the duty cycle of the inverter and the rail voltage of the power supply, the contactless power supply can energize a variety of different devices. The power supply can even energize several different devices at the same time. This ability to power a multitude of different devices overcomes many of the limitations previously associated with CEETS. Further, because the power supply can energize a variety of different devices, a central single source for supply power to a variety of small electronic devices is possible.

In one embodiment, a sensor may also coupled to the tank circuit. It would monitor various operational characteristics of the tank circuit, such as the phase of the current within the tank circuit. These operation characteristics are indicative of the total load energized by the power supply. When the operational characteristics indicate that the power supply is not efficiently supplying power to the load, the controller causes the power supply to seek an improved configuration.

The process of seeking an improved configuration may include one or more of the following steps. The power supply could automatically attempt to compensate by changing the frequency of the inverter and the duty cycle of the inverter. If this sufficiently correct the efficiency of the power supply, the controller causes the tank circuit to change its resonant frequency. As is well known, the resonant frequency of a tank circuit is in fact a range centered about a frequency. The tank circuit will resonate at frequencies which are approximately the resonant frequency. However, the adaptive power supply described herein reconfigures the tank circuit to have a substantially different resonant frequency.

The tank circuit may consist of either a variable inductor or a variable capacitor or both. The controller would then change the inductance of the variable inductor or the capacitance of the variable capacitor, or both, thus causing the tank circuit to have a different resonant frequency.

The controller may also establish a new rail voltage for the DC power source. It also sets a new inverter frequency and a new duty cycle for the inverter. The adaptive power supply then operates with the new configuration.

If the adaptive power supply is still not operating effectively, the power supply will once again attempt to rectify the problem by changing the frequency of the inverter and the duty cycle of the inverter. If the problem is still not corrected, then the power supply will repeat the process of reconfiguring the tank circuit, setting a new inverter frequency and setting a new duty cycle.

This power supply continually searches for the most efficient settings to deliver power to the devices. However, if none of the various settings delivers power efficiently to the devices, then the power supply will select the most efficient of the previous configurations and operate the power supply with those settings.

Thus, the power supply efficiently powers a variety of loads. Further, because the power supply is contactless, a user does not need to have a multitude of different power supplies or connectors.

These and other objects, advantages and features of the invention will be more readily understood and appreciated by reference to the detailed description of the drawings.

DETAILED DESCRIPTION OF THE DRAWINGS

The present invention provides an adaptive inductive ballast circuit in which the inductance and/or the capacitance of the power supply circuit is variable to provide a broad range of adaptability, thereby permitting the ballast circuit to power a variety of inductively powered devices with widely differing load characteristics. For purposes of disclosure, the present invention is described in connection with a resonance-seeking ballast circuit, and more particularly in connection with the inductive ballast described in U.S. patent application Ser. No. 10/246,155 entitled "Inductively Coupled Ballast Circuit," which incorporated by reference into this application in its entirety. The present invention is, however, well suited for use with other inductive ballast circuits.

Figure 1:
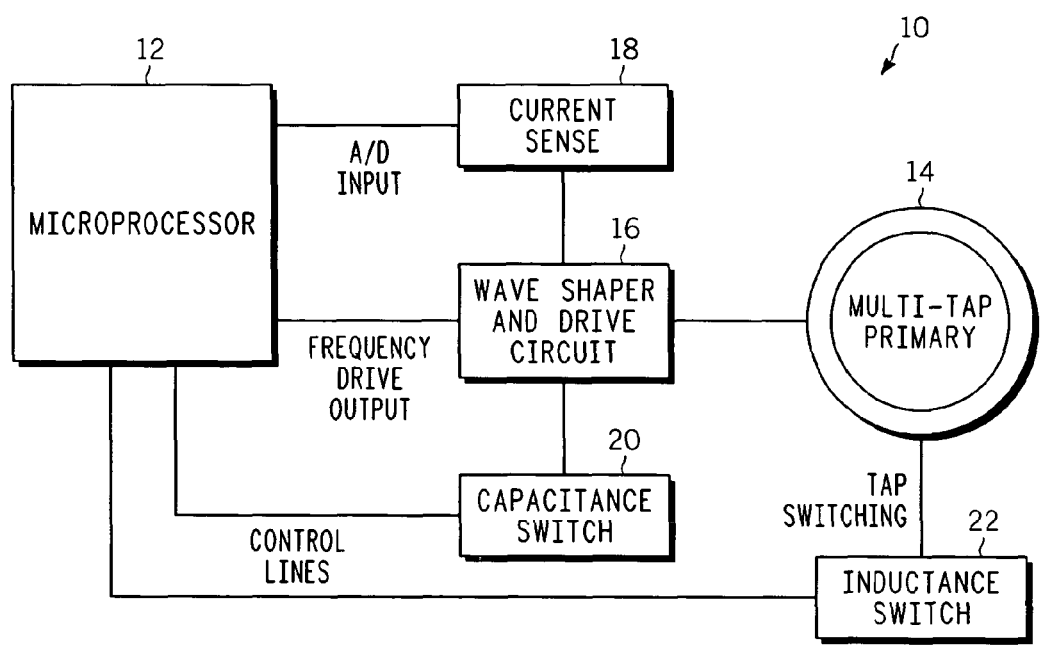
FIG. 1 is a block diagram of an adaptive inductive ballast in accordance with one embodiment of the present invention.

A block diagram showing the general construction of an adaptive inductive ballast 10 in accordance with one embodiment of the present invention is shown in FIG. 1. As illustrated, the adaptive inductive ballast 10 generally includes a microprocessor 12 that controls operation of the circuit, a multi-tap primary 14 for generating a magnetic field, a wave shaper and drive subcircuit 16 that generates the signal applied to the primary 14, a current sense subcircuit 18 that monitors the signal applied to the primary 14 and provides corresponding feedback to the microprocessor 12, a capacitance switch 20 for adjusting the capacitance values in the wave shaper and drive subcircuit 16, and an inductance switch 22 for adjusting the inductance of the multi-tap primary 14. The microprocessor is a conventional microprocessor widely available from a variety of suppliers.

The capacitance switch 20 generally includes two banks of capacitors and a plurality of switches, such as transistors, that are selectively actuatable by the microprocessor 12 to control the values of the two capacitor banks. The capacitors in each bank can be arranged in series or parallel depending on the desired range and distribution of possible capacitance values. The first bank of capacitors replace capacitor 271 of the pre-existing resonance-seeking ballast shown in the above referenced application. Similarly, the second back of capacitors replace capacitor 272 of the pre-existing resonance-seeking ballast shown in the above referenced patent application. In effect, the capacitance switch 20 makes capacitors 271 and 272 from the pre-existing resonance-seeking ballast into variable capacitors, the values of which are controlled by the microprocessor 12. Alternatively, the described capacitance switch 20 can be replaced by other circuitry capable of providing variable capacitance.

The inductance switch 22 generally includes a multi-tap primary 14 and a plurality of switches, such as transistors, that are selectively actuatable by the microprocessor 12 to control the values of the inductance of the primary 14. The multi-tap primary 14 replaces primary 270 of the pre-existing resonance-seeking ballast shown in the attached patent application. In effect, the inductance switch 22 makes primary 270 from the pre-existing resonance-seeking ballast into a variable inductance coil by varying the number of turns in the primary 14, the value of which is controlled by the microprocessor 12. Alternatively, the described inductance switch 22 can be replaced by other circuitry capable of providing variable inductance.

In general operation, the microprocessor 12 is programmed to receive input from the current sense subcircuit 18, which is indicative of the current applied to the primary 14. The microprocessor 12 is programmed to separately adjust the capacitance switch 20 and the inductance switch 22 to cycle through the range of capacitance values and inductance values available to the circuit. The microprocessor 12 continues to monitor the input from the current sense circuit 18 while adjusting the capacitance and inductance values to determine which values provide optimum current to the primary 14. The microprocessor 12 then locks the adaptive ballast into the optimum settings.

Figure 2:
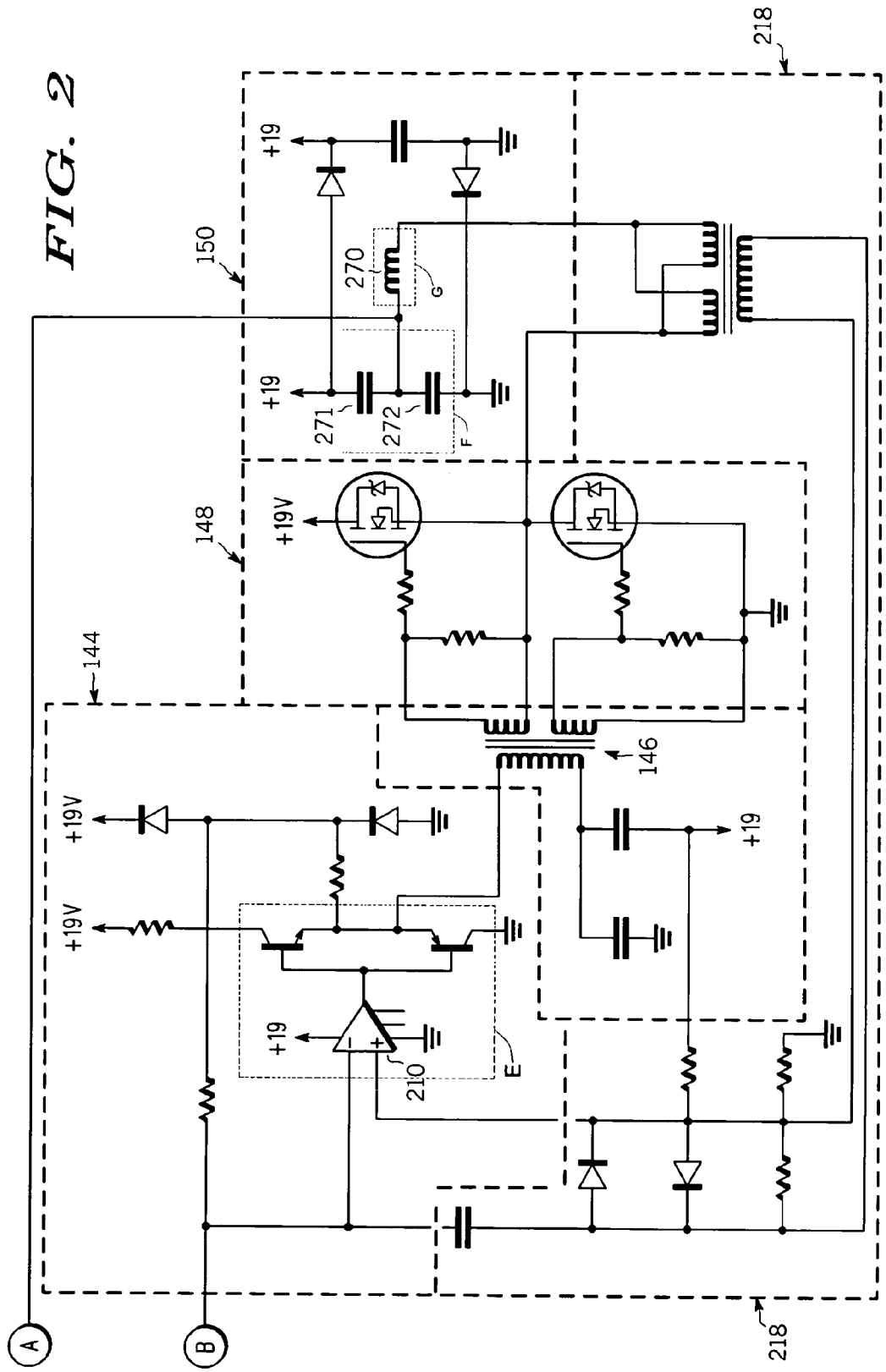
FIG. 2 is a schematic diagram of the resonance-seeking ballast of the attached patent application marked to show changes to incorporate the adaptive inductive ballast of the present invention.

Some of the changes required to adapt the resonance-seeking inductive ballast of the application patent application into an embodiment of the adaptive inductive ballast circuit 10 are noted in the schematic diagram of FIG. 2.

While the pre-existing resonance-seeking ballast is described in greater detail in U.S. patent application Ser. No. 10/246,155, an overview of the circuit may be helpful to a fuller understanding of this invention. A ballast feedback circuit is connected at point A and a control circuit is connected at point B. Oscillator 144 provides half bridge inverter 148 with an alternating signal by way of drive 146. Half bridge inverter powers tank circuit 150. Current sensing circuit 218 provides feedback to oscillator 144. The feedback circuit, control circuit, oscillator, half bridge inverter, drive and current sensing circuit 218 as well as other supporting circuitry is more fully described in the above referenced patent application.

In FIG. 2, a phase delay could be inserted at E and can be controlled as a delay line or even DSP (Digital Signal Processing) could be used to delay this signal. This delay can be used to throttle the phase and control secondary amplitude. At F, switched capacitance can adjust the resonant frequency based on the adjustable primary inductance. Simple transistors can be used to switch in and out capacitance. The capacitance is changed when the primary inductor changes as to match load. At G, primary inductance can be switched to adjust the power required by the secondary circuit. With that load information, the control processor can adjust the inductance as needed to provide the power required. The inductance can be switched using transistors and multiple taps from the primary inductor controlled by the microprocessor.

Figure 3:
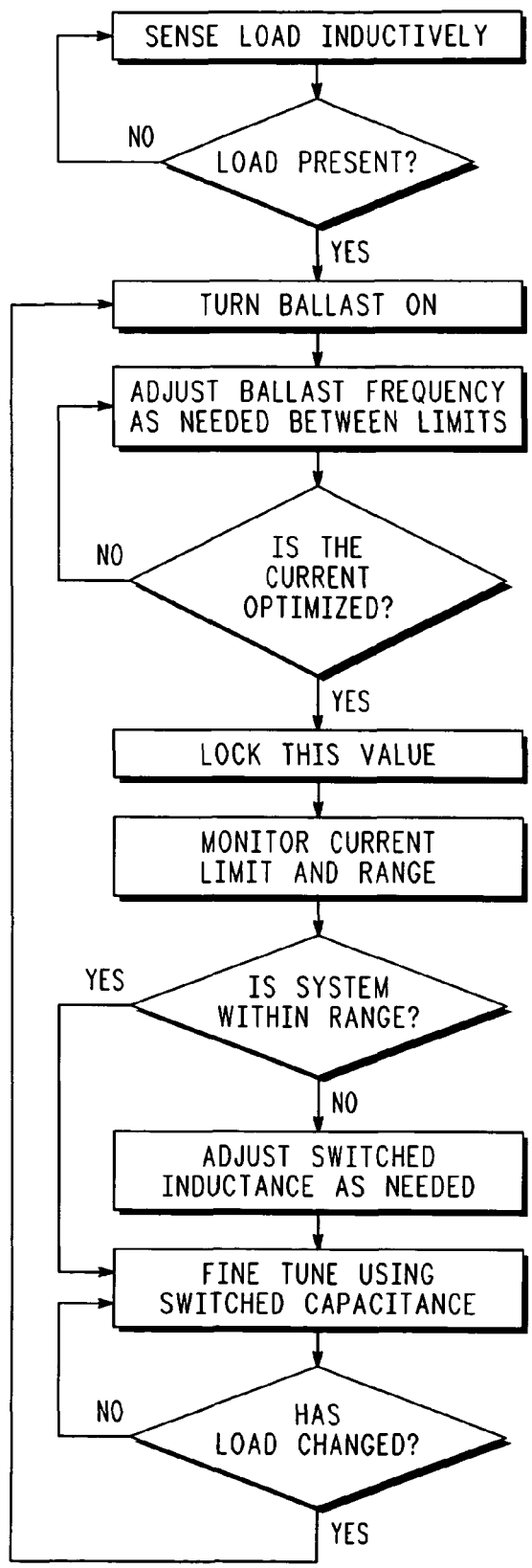
FIG. 3 is a flow chart illustrating operation of the adaptive inductive ballast.

The operating sequence of the adaptive inductive ballast circuit is described in more detail in connection with FIG. 3. In operation, the illustrated system waits until it determines that a load is present before applying power to the primary 14. This will save power and may be done by providing each inductively powered device with a magnet that actuates a reed switch adjacent to the primary. Alternatively, a user-actuated switch (not shown) may be provided so that the user can engage the power supply when an inductively powered device is present. As another alternative, the inductively powered device may be configured to mechanically actuate a switch when it is placed into located by the primary to signal its presence. As a further alternative, the switching mechanism can be eliminated and the ballast circuit can provide power to the primary 14 regardless of the presence of a load.

Once the power supply circuit is activated, the circuit adjusts its frequency to optimize the current applied to the primary. After the appropriate operating frequency has been determined at initial capacitance and inductance values, the microprocessor locks the ballast circuit into the operating frequency and then begins to cycle through the range of inductance values available through the multi-tap primary. After each change in inductance value, the microprocessor unlocks the operating frequency and permits the ballast circuit to seek resonance, settling at a frequency that provides optimal current to the primary. The microprocessor continues cycling through the available inductance values until it has determined which value provides optimal current to the primary. In one embodiment, a progressive scanning process is used to determine the appropriate inductance value. This is achieved by starting the scanning process with the lowest inductance value, and sequentially stepping up the inductance value until the change in inductance value results in a reduction in the current applied to the primary. The microprocessor will then step back down one inductance value, where the greatest current was achieved. Alternatively, the scanning process may begin with the highest inductance value, and sequentially step down the inductance value until the change in inductance value results in a reduction in the current applied to the primary. The microprocessor will then step back up one inductance value, where the greatest current was achieved. As another alternative, the microprocessor can step through each inductance value to determine the corresponding current, and after stepping through each value, return to the inductance value that provided the greatest current to the primary.

After the appropriate inductance value is determined, the microprocessor locks the circuit at the determined inductance value and begins to cycle through the capacitance values. In one embodiment, the microprocessor uses a progressive scanning technique to determine the capacitance that provides the primary with the greatest current. The scanning process may progress upwardly from the lowest capacitance value or downwardly from the highest capacitance value, as described above in connection with the scanning process for the inductance value. As an alternative to a progressive scanning process, the microprocessor can step through each capacitance value to determine the corresponding current, and after stepping through each value, return to the capacitance value that provided the greatest current to the primary.

In this embodiment, the frequency of the ballast circuit is not permitted to vary once the appropriate inductance value has been determined. The microprocessor can, alternatively, be programmed to permit the ballast circuit to seek resonance after each change in capacitance value.

In an alternative embodiment, the microprocessor may be programmed to provide adjustment of only the capacitance value or only the inductance value of the power supply circuit. In the former alternative, the multi-tap primary can be replaced by a conventional single-tap primary and the inductance switch can be eliminated. In the latter alternative, the capacitor bank can be replaced by a single set of capacitors and the capacitance switch can be eliminated. In another alternative embodiment, the microprocessor can be programmed to adjust the capacitance before adjusting the inductance.

As noted above, the present invention is not limited to use in connection with a resonance-seeking ballast. In other applications, a current sensor may be incorporated into the ballast to provide input to the microprocessor that is representative of the current being applied to the primary. In operation without a resonance-seeking ballast, the microprocessor will separately cycle through the various capacitance and inductance values to determine the values that provide optimum power to the primary.

In a further alternative embodiment, the adaptive inductive ballast 10 may include phase delay circuitry (not shown) that permits the ballast 10 to throttle the phase and control secondary amplitude. The phase delay circuitry may include a delay line or a Digital Signal Processor (DSP) that is connected to the wave shaper and drive circuit 16 following the operational amplifier 210.

Figure 4:
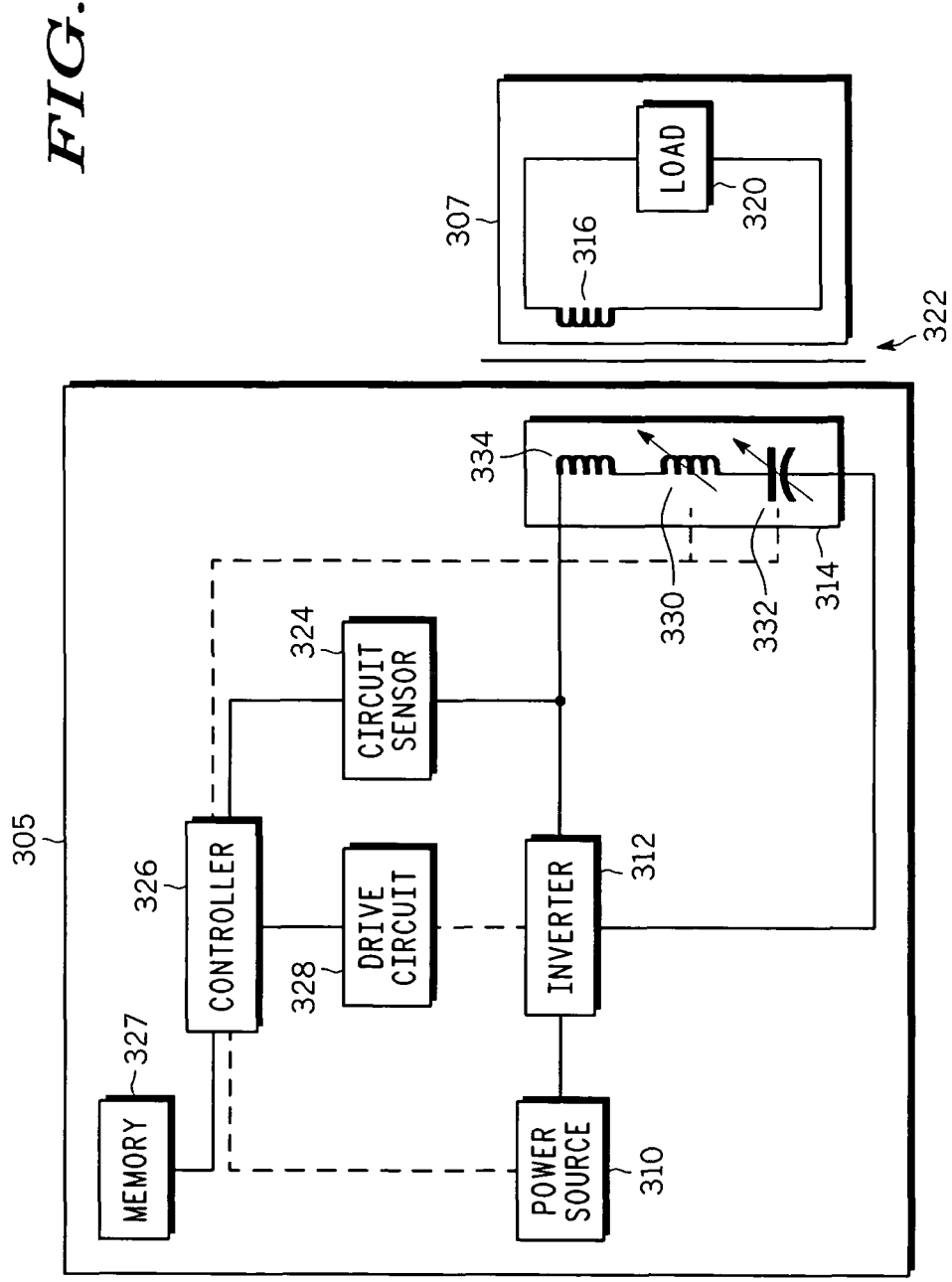
FIG. 4 is a block diagram for an adaptive contactless energy transmission system.

Further exemplifying the ideas and concepts expressed above, an additional embodiment for an adaptive contactless energy transmission system is shown in the block diagram of FIG. 4. The adaptive contactless energy transmission system is comprised of adaptive inductive power supply 305 and remote device 307.

As is well know, power source 310 is a DC power source providing DC (direct current) power to inverter 312. Inverter 312 converts the DC power to AC (alternating current) power. Inverter 312 acts as an AC power source supplying the AC power to tank circuit 314. Tank circuit 314 is inductively coupled to secondary winding 316 of remote device 307.

Secondary winding 316 of remote device 307 has no core. Line 322 indicates an air gap between remote device 307 and adaptive inductive power supply 305.

Remote device 307 has a load 320. Load 320 could include a rechargeable device, such as a micro-capacitor or a rechargeable battery. Alternatively, load 320 could be a lamp, radio or any other electrical device adapted to receive power from adaptive inductive power supply 305 whenever remote device 307 is placed in proximity of adaptive inductive power supply 305.

Circuit sensor 324 is coupled to the tank circuit 314 and inverter 312. Circuit sensor 324 is also coupled to controller 326. Circuit sensor 324 provides information regarding the operational parameters of adaptive inductive power supply 305. For example, circuit sensor 324 could be a current sensor used to provide controller 326 information regarding the phase, frequency and amplitude of the current in tank circuit 314.

Controller 326 could be any one of a multitude of commonly available microcontrollers programmed to perform the functions hereinafter described, such as the Intel 8051 or the Motorola 6811, or any of the many variants of those microcontrollers. Controller 326 could have a ROM (read only memory) and RAM (random access memory) on the chip. Controller 326 could have a series of analog and digital outputs for controlling the various functions within the adaptive inductive power supply.

Controller 326 is connected to memory 327. Controller 326 is also coupled to drive circuit 328. Drive circuit 328 regulates the operation of inverter 312, such as the frequency and timing of inverter 312. Drive circuit 328 could be constructed in a number of different manners. For example, driver circuit 328 could be constructed of discrete components such as transistors, resistors and capacitors; it could be a discrete integrated circuit designed to drive inverters; or it could be a functional component of controller 326 if controller 326 were a microcontroller.

Controller 326 is also coupled to power source 310. Controller 326 can manipulate the rail voltage of power source 310. As is well known, by altering the rail voltage of power source 310, the amplitude of the output of inverter 312 is also altered.

Finally, controller 326 is coupled to variable inductor 330 and variable capacitor 332 of tank circuit 314. Controller 326 could be a microcontroller, such as an 8051-type microcontroller. Alternatively, controller 326 could be a microprocessor with additional supporting circuitry.

Controller 326 can modify the inductance of variable inductor 330 or the capacitance of variable capacitor 332. This could be done, e.g., by switching in or out additional capacitor or inductors or by changing the physical characteristics of variable inductor 330 or variable capacitor 332. By modifying the inductance of variable inductor 330 and the capacitance of variable capacitor 332, the resonant frequency of tank circuit 314 can be changed.

By modifying the inductance of variable inductor 330 or the capacitance of variable capacitor 332, or both, tank circuit 314 may have a first resonant frequency and a second resonant frequency. Tank circuit 314 could also have several resonant frequencies. As used herein, the term "resonant frequency" refers to a band of frequencies within which tank circuit 314 will resonate. As is well known, a tank circuit will have a resonant frequency, but will continue to resonate within a range of frequencies.

Variable inductor 330 could be a thyristor controlled variable inductor, a compressible variable inductor, parallel laminated core variable inductor, a series of inductors and switches capable of placing select fixed inductors into tank circuit 314, or any other controllable variable inductor. Variable capacitor 332 could be a switched capacitor array, a series of fixed capacitors and switches capable of placing select fixed capacitors into tank circuit 314, or any other controllable variable capacitor.

Tank circuit 314 also includes primary winding 334. Primary winding 334 and variable inductor 330 are shown separate. Alternatively, primary winding 334 and variable inductor 330 could be combined into a single element.

Tank circuit 314 is shown as a series resonant tank circuit. A parallel resonant tank circuit could also be used.

Figure 5A:
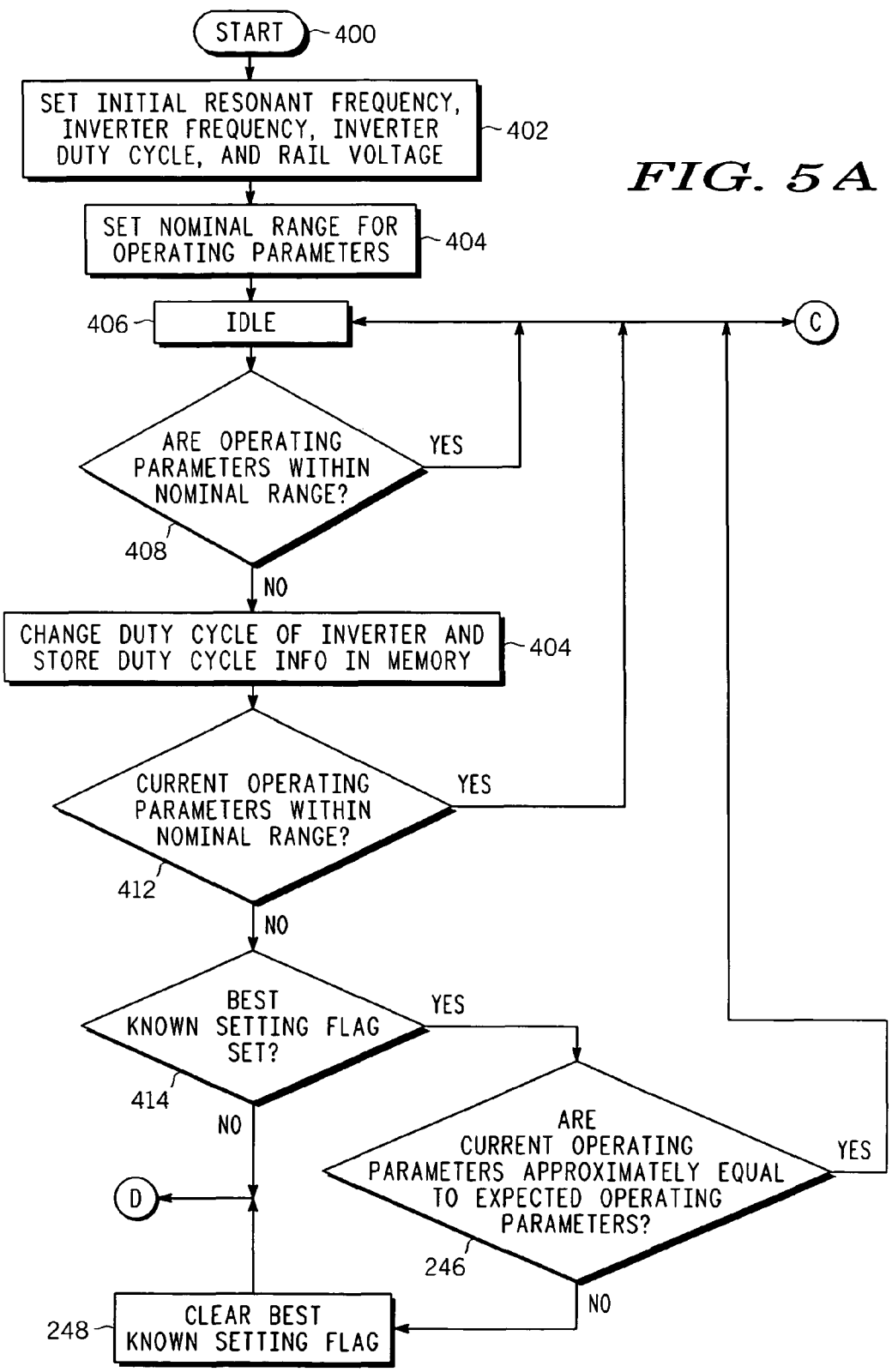
FIGS. 5A and 5B are a flow chart showing the operating of an adaptive contactless energy transmission system.
Figure 5B:
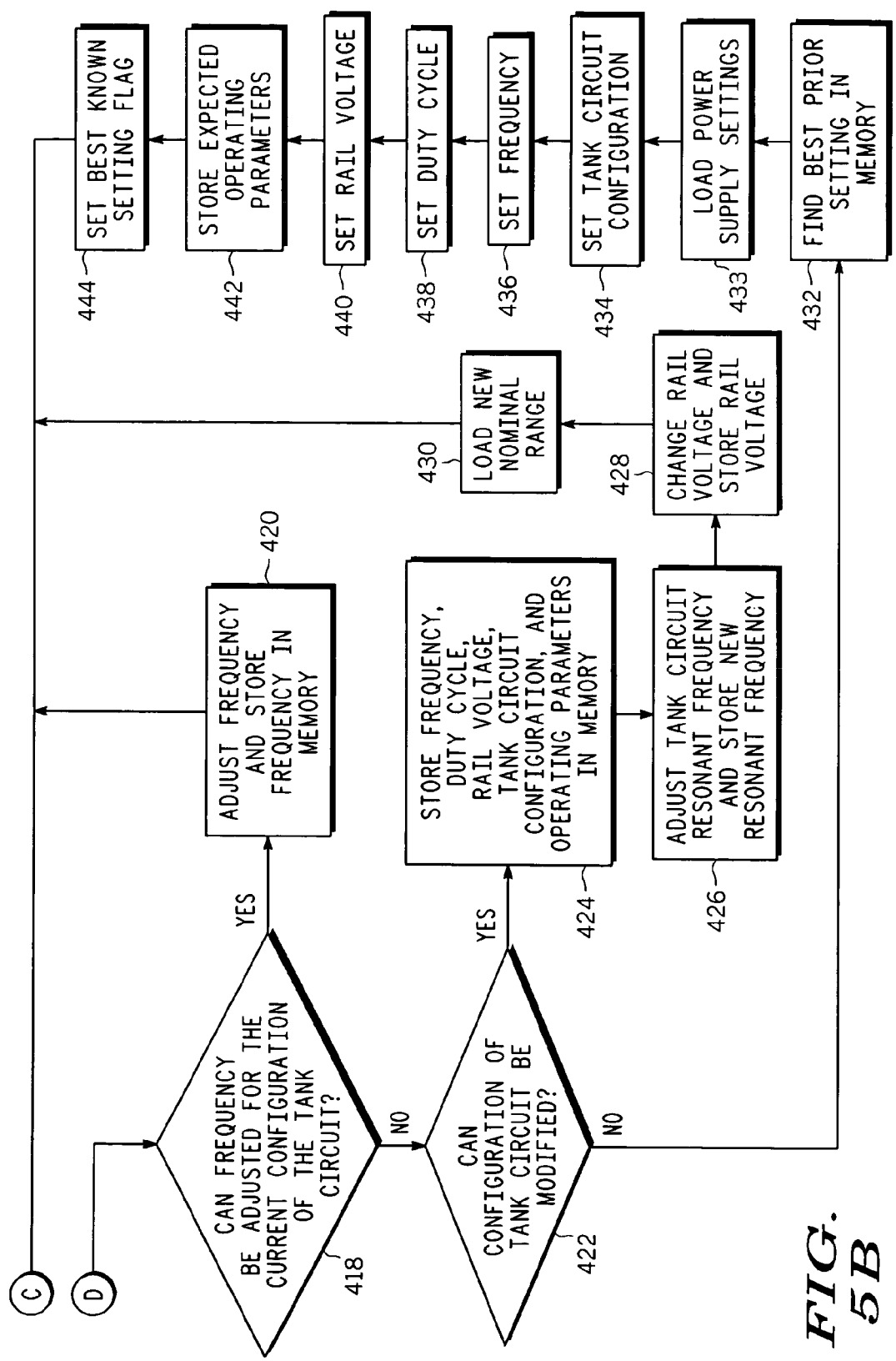

FIGS. 5A and 5B show a flow chart showing the operation of adaptive inductive power supply 305 of adaptive contactless energy transmission system shown in FIG. 4.

When turned on (step 400), controller 326 initializes the resonant frequency of tank circuit 314 by setting the inductance of variable inductor 330 and the capacitance variable capacitor 332 so that tank circuit 314 operates at a pre-selected initial resonant frequency. Step 402. Controller 326 initializes drive circuit 328 to operate at a pre-selected frequency with a pre-selected phase offset. Controller 326 initializes power source 310 to operate at a predetermined rail voltage. Step 402.

In order to conserve power, when adaptive inductive power supply 305 is initially energized, adaptive inductive power supply 305 might be initialized to supply power at a very low level. Alternatively, adaptive inductive power supply 305 might be initialized to supply power at a more moderate level to accommodate some common remote devices.

Controller 326 then sets the nominal range for the operating parameters. Step 404. The operating parameters for the power supply are various measures of current and voltage throughout the system. For example, the peak to peak inverter voltage, the RMS current flowing through the primary winding, and the phase offset of the current flowing through the primary winding are all operating parameters. For example, the operating range could include a range of the phase offset between the inverter voltage and the voltage current, a range for the current amplitude, and a range for the inverter output voltage. As a further example, an operating range could be an inverter voltage from 5 Volts to 5.3 volts, with a current phase offset of no more than 20 degrees, and a current amplitude of between ½ and 1 amp.

The nominal range is the acceptable range of possible values for the operating parameters. If an operating parameter are not within the nominal range, then the power supply is not operating efficiently.

Returning to FIG. 5, the system then idles. Step 406. Controller 326 continually monitors the operating parameters of adaptive inductive power supply 305. If the operating parameters fall within the nominal range, then the circuit continues to idle. Step 408.

When remote device 307 is placed near primary winding 334, then power is drawn from adaptive inductive power supply 305. As a result, the operating parameters change. If the operating parameters fall outside of the nominal range, then controller 326 reconfigures adaptive inductive power supply 305.

If adaptive inductive power supply 305 had an initially low power setting, adaptive inductive power supply 305 would thus sense the presence of the remote device, and automatically increase power to a more moderate level.

Obviously, reconfiguration of adaptive inductive power supply 305 could be triggered by one operating parameter falling outside of the nominal range, or reconfiguration of adaptive inductive power supply 305 could be triggered by a combination of operating parameters falling outside of the nominal range. It is satisfactory to monitor only the phase of the current flowing through the primary winding. However, various enhancements where other operating parameters are measured and weighted together could be readily conceived.

First, controller 326 causes drive circuit 328 to alter the duty cycle of inverter 312. Step 410. The duty cycle of inverter 312 is altered, and the altered duty cycle is stored in memory 327.

The operating parameters are again measured. Step 412. If the operating parameters are still outside of the nominal range, then a 'best known setting' flag is checked. Step 414. The 'best known setting' flag is discussed below.

If the "best know setting flag" is not set, then controller 326 determines whether the inverter frequency can be adjusted and still maintain resonance within tank circuit 314. Step 418. Controller 326 first finds the maximum and minimum resonant frequency of tank circuit 314.

The maximum and minimum resonant frequency of tank circuit 314 for any particular configuration of variable inductor 330 and variable capacitor 332 could be stored in memory 327. In the alternative, the maximum and minimum resonant frequency of tank circuit 314 could be calculated from the inductance of primary winding 334, the inductance of variable inductor 330, and the capacitance of variable capacitor 332. Controller 326 then compares the maximum and minimum resonant frequency of tank circuit 314 with the current operating frequency of inverter 312.

If possible, then controller 326 causes drive circuit 328 to adjust the inverter frequency and stores the new inverter frequency in memory 327. Step 420. The circuit returns to the idle state. Step 406. If the inverter frequency cannot be adjusted within the resonant frequency of the current configuration of tank circuit 314, then controller 326 determines whether the configuration of tank circuit 314 can be modified. Step 422.

If it can be modified, then controller 326 stores the current frequency, duty cycle, rail voltage, tank circuit configuration, and operating parameters in memory 327. Step 424. It then adjust the tank circuit resonant frequency. Step 426. Adjustment of the tank circuit resonant frequency is accomplished by changing the inductance of variable inductor 330 and the capacitance of variable capacitor 332.

The rail voltage could then be changed. Step 428. Since the resonant frequency of tank circuit 314 has been altered, a new nominal range for the operating parameters is calculated or loaded from memory 327. Step 430. The power supply then returns to idle. Step 406.

If the configuration of tank circuit 314 can not be further modified, then controller 326 searches for the best prior configuration. Step 432. Controller 326 compares the operating parameters previously stored and selects the best configuration.

After selecting the best configuration, controller 326 retrieves various settings of adaptive inductive power supply 305 from memory for that configuration. Step 433. Controller 326 then sets the configuration of tank circuit 314 by setting the inductance of adjustable inductor 30 and capacitance of adjustable capacitor 32. Step 434. Controller 326 then sets the frequency of inverter 312. Step 436. Controller 326 then sets the duty cycle of inverter 312. Step 438. Controller 326 sets the rail voltage of power source 310. Step 440.

Controller 326 then stores the expected operating parameters in memory 327. Step 442. Alternatively, controller 326 could set a pointer to the expecting operating parameters in memory 327. Controller 326 then sets the 'best known setting' flag. Step 444. The power supply then returns to the idle state. Step 406. The 'best known setting' flag is an indication to controller 326 that the current settings being used by adaptive inductive power supply 305 are the best available.

If the 'best known setting' flag is set, then the system is operating at its best settings even though the operating parameters are outside of the nominal range. Further changes to the inverter frequency, resonant circuit frequency, inverter duty cycle or rail voltage thus would not result in any improvement to the system. With the 'best known setting' flag set, the system checks if the operating parameters are approximately equal to the expected operating parameters.

Thus, if the best known setting flag is set (See Step 414), controller 326 checks whether the current operating parameters are approximately the same as the expected operating parameters. Step 446. If so, then further adjustments to power supply will not result in any improved performance, and therefore the system merely returns to the idle state. Step 406.

If, on the other hand, the current operating parameters are not approximately equal to the expected operating parameters, then the best known setting flag is cleared. Step 448. The process of reconfiguring adaptive inductive power supply 305 continues. Step 422.

The adaptive contactless energy transmission system described thus can dynamically handle a variety of different devices. Adaptive inductive power supply 305 automatically adjusts to different devices with different loads, and continually determines and optimal operating configuration for the power supply.

Further, more than a single device can be simultaneously powered by adaptive inductive power supply 305. As new devices are placed near adaptive inductive power supply 305, controller 326 continually adjusts the operating parameters of adaptive inductive power supply 305 to maintain efficiency. This allows for one single power supply to provide power to a multitude of different devices. The devices need not be located immediately adjacent adaptive inductive power supply 305. That can be spaced at different distances away from adaptive inductive power supply 305. For example, it is possible to construct a power supply whereby sealed lights are stacked near adaptive inductive power supply 305 and each light will be illuminated even though the distance from adaptive inductive power supply 305 is different for each light.

The above description is of the preferred embodiment. Various alterations and changes can be made without departing from the spirit and broader aspects of the invention as defined in the appended claims, which are to be interpreted in accordance with the principles of patent law including the doctrine of equivalents. Any references to claim elements in the singular, for example, using the articles "a," "an," "the," or "said," is not to be construed as limiting the element to the singular.

The invention claimed is:

1. A contactless power supply for supplying power wirelessly to an electrically powered remote device comprising:
   a tank circuit having a primary for transferring power to the electrically powered remote device by an inductive coupling, said electrically powered remote device having a secondary in electrical communication with a load;
   drive circuitry configured to control application of power to said tank circuit, wherein operation of said drive circuitry varies based on a control signal applied to a control input of said drive circuitry; and
   a control system coupled to said drive circuitry, said control system configured to control said control signal to direct operation of said drive circuitry, said control system configured to vary power by selectively changing a phase delay of said control signal provided to said drive circuitry.

2. The contactless power supply of claim 1 wherein said control system includes a digital signal processor configured to insert said phase delay.

3. The contactless power supply of claim 1 further comprising a sensor operatively coupled to the tank circuit and configured to generate sensed information.

4. The contactless power supply of claim 3 wherein said sensed information is a characteristic of power in said tank circuit, and wherein said characteristic of power includes at least one of current, voltage, and phase in said tank circuit.

5. The contactless power supply of claim 3 wherein said control system includes a controller configured to vary power based on said sensed information and phase delay circuitry configured to vary power by selectively inserting said phase delay, wherein selectively changing the phase delay includes controlling the phase delay to throttle a phase.

6. The contactless power supply of claim 5 wherein:
   said control system includes a wave shaper and said phase delay circuitry includes a digital signal processor;
   said digital signal processor, said wave shaper, and said drive circuitry are configured to selectively insert said phase delay and generate a signal applied to said tank circuit.

7. The contactless power supply of claim 5 wherein said phase delay circuitry is operatively coupled to said drive circuitry, wherein said phase delay circuitry is configured to vary power by throttling the phase.

8. The contactless power supply of claim 1 wherein said phase delay circuitry is coupled to feedback corresponding to a characteristic of power in said tank circuit.

9. The contactless power supply of claim 8 wherein said control system is configured to vary, based on said feedback, at least one of a resonant frequency of said tank circuit, a duty cycle of said drive circuitry, a rail voltage of said power applied to said tank circuit, and an operating frequency of said drive circuitry.

10. The contactless power supply of claim 1 wherein said control system is configured to throttle a phase to control amplitude of power wirelessly supplied to a secondary.

11. The contactless power supply of claim 1 wherein said control system is configured to control said phase delay as a delay line.

12. The contactless power supply of claim 1 wherein said control system is configured to vary power by throttling a phase.

13. A method of operating an inductive power supply to supply wireless power from a primary to an electrically powered remote device, the method including the steps of:
providing a control signal to switching circuitry of the inductive power supply to control application of power to the primary, wherein operation of the switching circuitry varies based on the control signal;
establishing, based on application of power to the primary, an inductive coupling between the primary of the inductive power supply and a secondary of the electrically powered remote device, wherein the secondary of the electrically powered remote device is in electrical communication with a load;
transferring power to the electrically powered remote device via the inductive coupling;
varying power transferred to the electrically powered remote device via the inductive coupling; and
selectively changing, in the inductive power supply, a phase delay of the control signal provided to the switching circuitry to vary power transferred wirelessly to the electrically powered remote device.

14. The method of claim 13 further including:
sensing, in the inductive power supply, a characteristic of power of the inductive coupling; and
based on the sensed characteristic of power, varying power transferred to the electrically powered remote device.

15. The method of claim 13 wherein said selectively changing the phase delay includes inserting and controlling the phase delay to throttle a phase.

16. The method of claim 15 wherein inserting and controlling the phase delay to throttle the phase affects amplitude of power wirelessly supplied to a secondary.

17. The method of claim 13 wherein said selectively changing includes controlling the phase delay as a delay line.

18. The method of claim 13 further comprising varying power transferred to the electrically powered remote device and selectively inserting the phase delay.

19. The method of claim 13 further comprising generating a signal applied to a tank circuit for transferring power to the electrically powered remote device.

20. The method of claim 19 further comprising receiving feedback corresponding to a characteristic of power in the tank circuit, and varying the signal applied to the tank circuit in response to the feedback.

21. The method of claim 20 wherein said varying power includes varying, in response to the feedback, at least one of a duty cycle of the signal applied to the tank circuit, a rail voltage of the signal applied to the tank circuit, and an operating frequency of the signal applied to the tank circuit.

22. An inductive power supply system comprising:
an inductive power supply including:
a tank circuit having a primary configured to transfer power via an inductive coupling;
drive circuitry configured to control application of power to said tank circuit, wherein operation of said drive circuitry varies based on a control signal applied to a control input of said drive circuitry;
a control system coupled to said drive circuitry, said control system configured to control said control signal to direct operation of said drive circuitry and configured to vary power by selectively changing a phase delay of said control signal provided to said drive circuitry;
an electrically powered remote device separable from said inductive power supply, said electrically powered remote device including:
a receiver configured to receive power from said inductive power supply via said inductive coupling;
a load operatively coupled to said receiver, wherein said receiver provides said power to said load; and
wherein selectively changing said phase delay of the control signal controls power wirelessly supplied to said receiver via said inductive coupling.

23. The inductive power supply system as claimed in claim 22 wherein said inductive power supply further includes a sensor operatively coupled to said tank circuit and configured to generate sensed information.

24. The inductive power supply system as claimed in claim 23 wherein said sensed information is a characteristic of power in said tank circuit, and wherein said characteristic of power includes at least one of current, voltage, and phase in said tank circuit.

25. The inductive power supply system as claimed in claim 24 wherein said electrically powered remote device affects said sensed information.

26. The inductive power supply system as claimed in claim 22 wherein said control system includes:
a controller coupled to said drive circuitry and said sensor, said controller configured to vary power based on said sensed information; and
phase delay circuitry coupled to said drive circuitry, said phase delay circuitry configured to vary power by selectively inserting a phase delay.

27. The inductive power supply system of claim 22 wherein said receiver includes a secondary configured to form said inductive coupling with said tank circuit.

28. The inductive power supply system of claim 22 wherein said selective changing includes inserting a phase delay to throttle a phase.

29. The inductive power supply system of claim 28 wherein inserting a phase delay to throttle said phase affects amplitude of power wirelessly supplied to said receiver.

* * * * *